(12) United States Patent
Biedermann et al.

(10) Patent No.: US 8,506,610 B2
(45) Date of Patent: Aug. 13, 2013

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(75) Inventors: Lutz Biedermann, VS-Villingen (DE); Wilfried Matthis, Weisweil (DE); Berthold Dannecker, St. Georgen (DE)

(73) Assignee: Bierdermann Technologies GmbH & Co. KG, Donaueschingen (DE)

( * ) Notice: Subject to any disclaimer, the term of this patent is extended or adjusted under 35 U.S.C. 154(b) by 605 days.

(21) Appl. No.: 12/645,335

(22) Filed: Dec. 22, 2009

(65) Prior Publication Data
US 2010/0160976 A1    Jun. 24, 2010

Related U.S. Application Data

(60) Provisional application No. 61/140,612, filed on Dec. 23, 2008.

(30) Foreign Application Priority Data

Dec. 23, 2008 (EP) ...................................... 08022389

(51) Int. Cl.
*A61B 17/86* (2006.01)
*A61B 17/70* (2006.01)

(52) U.S. Cl.
USPC ........... 606/308; 606/305; 606/328; 606/267; 606/269

(58) Field of Classification Search
USPC .................. 606/305–308, 319, 328, 266–269
See application file for complete search history.

(56) References Cited

U.S. PATENT DOCUMENTS

| | | | |
|---|---|---|---|
| 5,578,033 A | 11/1996 | Errico et al. | |
| 5,584,834 A | 12/1996 | Errico et al. | |
| 5,586,984 A | 12/1996 | Errico et al. | |
| 5,609,593 A | 3/1997 | Errico et al. | |
| 5,672,176 A | 9/1997 | Biedermann et al. | |
| 5,728,098 A | 3/1998 | Sherman et al. | |
| 6,010,503 A | 1/2000 | Richelsoph et al. | |
| 6,254,602 B1 | 7/2001 | Justis | |
| 6,273,888 B1 * | 8/2001 | Justis ............................ 606/272 |

(Continued)

FOREIGN PATENT DOCUMENTS

| | | |
|---|---|---|
| EP | 2 022 423 A1 | 2/2009 |
| WO | WO 00/72769 A1 | 12/2000 |

(Continued)

*Primary Examiner* — Eduardo C Robert
*Assistant Examiner* — Julianna N Harvey
(74) *Attorney, Agent, or Firm* — Christie, Parker & Hale, LLP

(57) ABSTRACT

A receiving part for receiving a rod for coupling the rod to a bone anchoring element, the receiving part including: a receiving part body including a rod receiving portion with a channel for receiving a rod, and a head receiving portion for accommodating a head of a bone anchoring element, the head receiving portion having an open end and being flexible for inserting and clamping of the head; a locking ring around the head receiving portion to exert a first force onto the head receiving portion to lock the head therein; and a pre-locking ring separate from the locking ring and around the head receiving portion to exert a second force less than the first force onto the head receiving portion to clamp the head in a temporary pre-locking position.

25 Claims, 5 Drawing Sheets

(56) References Cited

U.S. PATENT DOCUMENTS

| | | |
|---|---|---|
| 6,355,040 B1 | 3/2002 | Richelsoph et al. |
| 6,582,436 B2 | 6/2003 | Schlapfer et al. |
| 7,090,674 B2 | 8/2006 | Doubler et al. |
| 7,585,315 B2 | 9/2009 | Donath |
| 2002/0032443 A1 | 3/2002 | Sherman et al. |
| 2003/0023240 A1* | 1/2003 | Amrein et al. .................. 606/61 |
| 2005/0080415 A1 | 4/2005 | Keyer et al. |
| 2005/0080420 A1 | 4/2005 | Farris et al. |
| 2005/0228392 A1 | 10/2005 | Keyer et al. |
| 2006/0161153 A1 | 7/2006 | Hawkes et al. |
| 2006/0200128 A1 | 9/2006 | Mueller |
| 2007/0093817 A1 | 4/2007 | Barrus et al. |
| 2007/0270839 A1 | 11/2007 | Jeon et al. |
| 2008/0009862 A1 | 1/2008 | Hoffman |
| 2008/0027432 A1 | 1/2008 | Strauss et al. |
| 2008/0108992 A1 | 5/2008 | Barry et al. |
| 2008/0119857 A1 | 5/2008 | Potash et al. |
| 2008/0234761 A1 | 9/2008 | Jackson |
| 2008/0243193 A1 | 10/2008 | Ensign et al. |
| 2009/0036934 A1 | 2/2009 | Biedermann et al. |
| 2009/0062867 A1 | 3/2009 | Schumacher |
| 2009/0105716 A1 | 4/2009 | Barrus |
| 2009/0105756 A1 | 4/2009 | Richelsoph |
| 2009/0105769 A1 | 4/2009 | Rock et al. |
| 2009/0105770 A1 | 4/2009 | Berrevoets et al. |
| 2009/0143827 A1 | 6/2009 | Levy et al. |
| 2009/0149887 A1 | 6/2009 | Schlaepfer et al. |
| 2010/0114180 A1* | 5/2010 | Rock et al. .................... 606/308 |

FOREIGN PATENT DOCUMENTS

| | | |
|---|---|---|
| WO | WO 00/72770 A1 | 12/2000 |
| WO | WO 2004/089245 A2 | 10/2004 |
| WO | WO 2007/011431 A2 | 1/2007 |
| WO | WO 2007/038350 A2 | 4/2007 |
| WO | WO 2007/038351 A2 | 4/2007 |

* cited by examiner

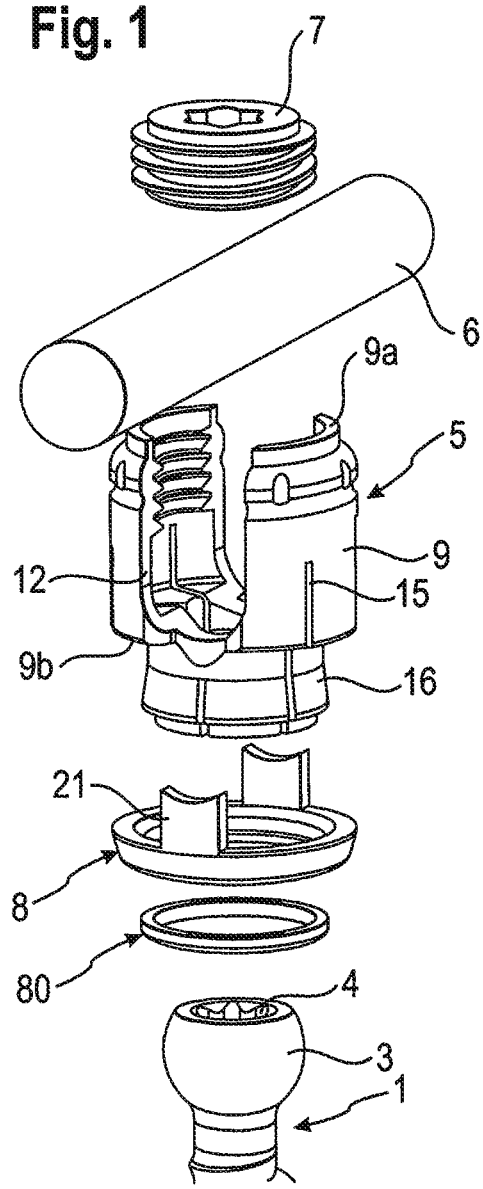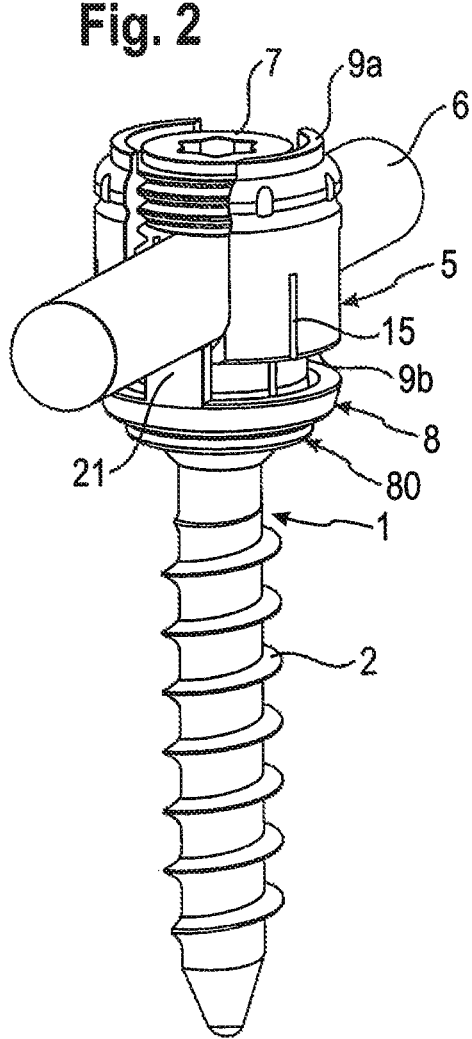

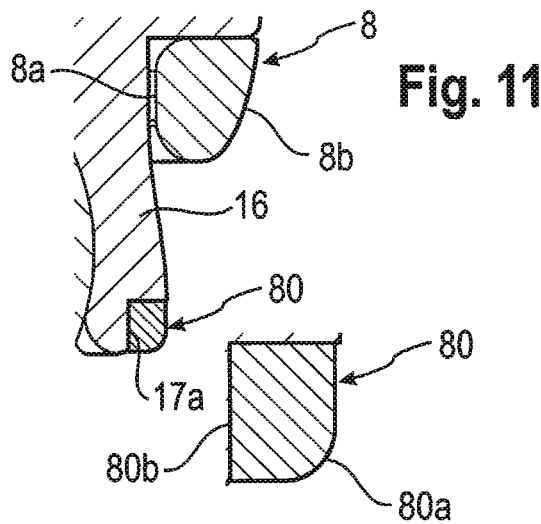
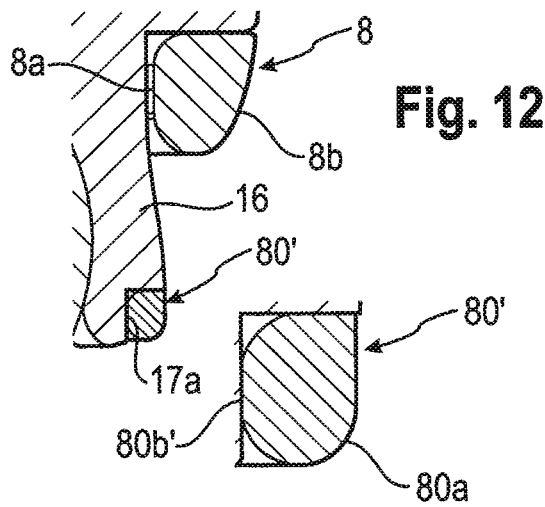
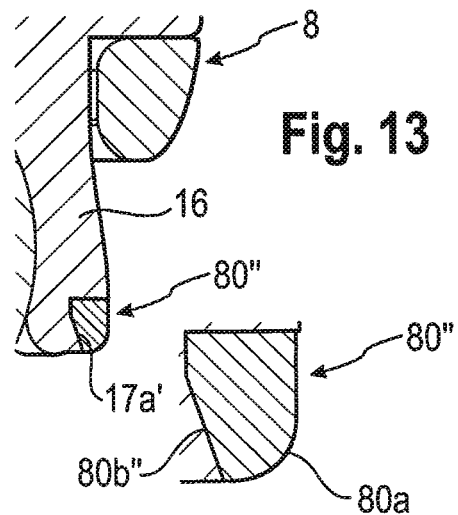
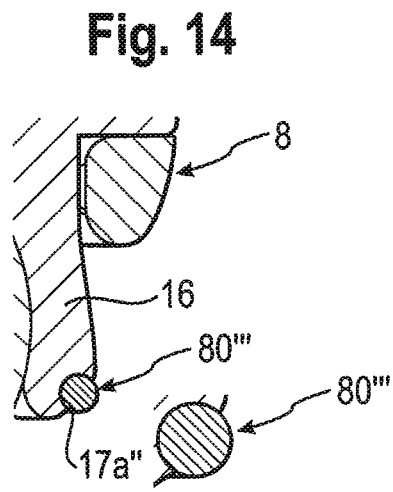

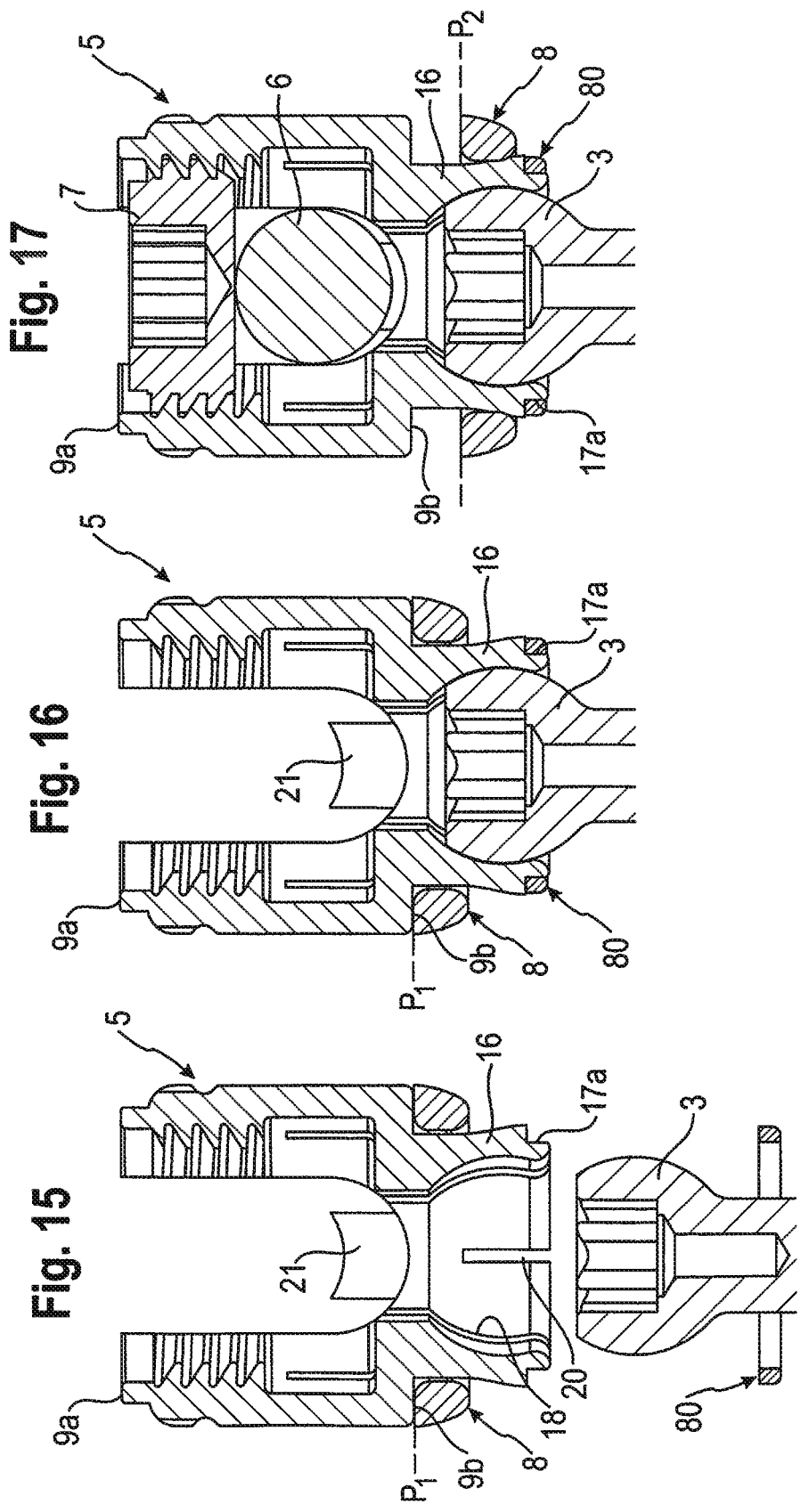

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATIONS

The present application claims priority to and the benefit of U.S. Provisional Patent Application Ser. No. 61/140,612, filed Dec. 23, 2008, the contents of which are hereby incorporated by reference in their entirety, and claims priority from European Patent Application EP 08 022 389.4, filed Dec. 23, 2008, the contents of which are hereby incorporated by reference in their entirety.

BACKGROUND

1. Field of the Invention

The invention relates to a receiving part for receiving a rod for coupling the rod to a bone anchoring element and a bone anchoring device with such a receiving part. The head of the bone anchoring element is locked in the receiving part by compression of a head receiving portion of the receiving part laterally surrounding the head by means of a locking ring. The receiving part further comprises a pre-locking ring for clamping the head by the pre-stress exerted onto the head receiving portion for safe handling during surgery. The locking ring is movable to a final locking position for locking the head. The bone anchoring device can be realized, for example, in the form of a polyaxial bone screw.

2. Description of Related Art

Various designs of polyaxial bone screws wherein the head is clamped from the side to lock the rotational position of the bone screw are known.

U.S. Pat. No. 5,672,176 describes a bone screw with a receiving part with a conically shaped seat and a conically shaped pressure element which exerts pressure onto the head from above and from the side. If the cone angle has a value laying within a specific range self-locking of the pressure element within the receiving part takes place which allows to preliminary lock the head within the receiving part while the rod is still movable in order to allow the adjustment of its position.

U.S. Pat. No. 5,728,098 describes a bone screw for connection to a spinal rod comprising a screw element and a receiver member which has slits provided at the bottom of the rod receiving channel and wherein two ring-shaped compression members made of a shaped-memory alloy are provided at the lower side and the upper side of the receiver member, respectively. The compression members contract about the portions of the receiver member when the temperature is elevated so that the rod is clamped in the channel.

WO 2007/038350 A2 discloses an apparatus for connecting a bone anchor to a support rod, the apparatus including a connector body and a cap. The connector body has a socket for insertion, angulation and removal of a bone anchor. A sleeve is provided which is configured to fit over the connector body in a temporary position in which the sleeve permits insertion of the bone anchor, to move to a provisional locking position in which the sleeve permits angulation but prevents removal of the bone anchor, and to move to a locking position in which the sleeve prevents both angulation and removal of the bone anchor. The sleeve extends over the whole length of the socket.

SUMMARY

It is the object of the invention to provide an improved receiving part for receiving a rod for coupling the rod to a bone anchoring element and a bone anchoring device with such a receiving part, which has a small size while simultaneously providing for safer handling during surgery and a safer and more secure final locking.

A pre-locking ring pre-locks a head of a bone anchoring element in a head receiving portion of a receiving part body which prevents removal of the head from the receiving part body and/or prevents movement of the head with respect to the receiving part body during surgery. This allows for safer handling of the bone anchoring device during surgery.

The receiving part and the bone anchoring device according to an exemplary embodiment of the invention comprises few elements, which reduces the costs of manufacturing and which facilitates handling. It makes use of the principle of clamping the head of the bone anchoring element circumferentially from the lateral sides, which reduces the force necessary to safely clamp the head. The design of the receiving part allows to further reduce the dimension in terms of height as well as in terms of the bottom outer diameter which is particularly suitable for applications where small-sized anchoring devices are utilized, such as in the field of cervical spinal surgery or paediatric applications, trauma and minimally invasive applications.

By providing various bone anchors with different receiving parts, a modular system is available prior to surgery.

Since the height of the locking ring is smaller than the height of the head receiving portion the receiving part has a profile with a small diameter. The pressure exerted via the locking ring onto the head receiving portion is largest at a position of the largest diameter of the head of the bone anchoring element. Therefore, the locking ring does not have to extend up to the open end of the head receiving portion which allows for a locking ring with a reduced diameter at the bottom end.

The locking ring is movable between a position in which the head is not clamped and a position in which the head is locked. The locking ring can be releasably held in either of the two end positions which makes handling convenient.

When the locking ring has a curved interior surface portion, jamming between the locking ring and the head receiving portion does not occur.

BRIEF DESCRIPTION OF THE DRAWINGS

Further features and advantages of the invention will become apparent from the description of embodiments using the accompanying drawings. In the drawings:

FIG. 1 shows a perspective exploded view of an embodiment of the bone anchoring device.

FIG. 2 shows a perspective view of the bone anchoring device of FIG. 1 in an assembled state.

FIG. 11 shows an enlarged portion of a cross-sectional view of the receiving part of FIGS. 1 and 2 with a further enlarged section of a pre-locking ring in a first embodiment.

FIG. 12 shows an enlarged portion of a cross-sectional view of the receiving part of FIGS. 1 and 2 with a further enlarged section of a pre-locking ring in a second embodiment.

FIG. 13 shows an enlarged portion of a cross-sectional view of an embodiment of a receiving part with a further enlarged section of a pre-locking ring in a third embodiment.

FIG. 14 shows an enlarged portion of a cross-sectional view of another embodiment of a receiving part with a further enlarged section of a pre-locking ring in a fourth embodiment.

FIG. 15 shows a cross-sectional view of an embodiment of a bone anchoring device in a first position.

FIG. 16 shows a cross-sectional view of the embodiment of the bone anchoring device of FIG. 15 in a second position.

FIG. 17 shows a cross-sectional view of the embodiment of the bone anchoring device of FIG. 15 in a third position.

DETAILED DESCRIPTION

Figure 3:
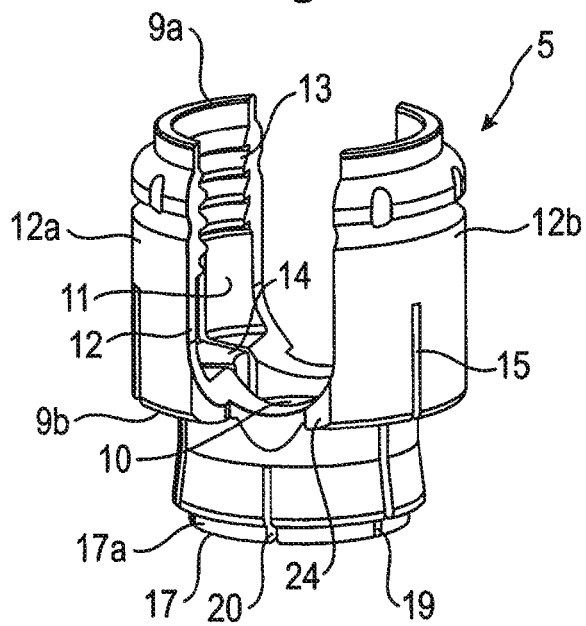
FIG. 3 shows a perspective view of the receiving part body according to a first embodiment.

As shown in FIGS. 1 and 2, the bone anchoring device according to one embodiment comprises a bone anchoring element 1 in the form of a bone screw having a threaded shaft 2 and a head 3 with a curved surface portion, in this embodiment a spherical segment-shaped head. The head 3 has a recess 4 for engagement with a screwing-in tool. The bone anchoring device further comprises a receiving part body 5 for receiving a rod 6 to connect it to the bone anchoring element 1. Further, a closure element 7 in the form of an inner screw is provided for securing the rod 6 in the receiving part body 5. In addition, the bone anchoring device includes a locking ring 8 for locking the head 3 in the receiving part body 5, and a pre-locking ring 80 for pre-locking the head 3 in the receiving part body 5.

As can be seen in particular in FIGS. 3 to 6, the receiving part body 5 comprises a rod receiving portion 9 which is substantially cylindrical and which has a first end 9a and a second end 9b opposite the first end 9a. The rod receiving portion 9 has a coaxial first bore 10 provided at the second end 9b. The diameter of the first bore 10 is smaller than the diameter of the head 3 of the bone anchoring element 1. The rod receiving portion 9 also comprises a coaxial second bore 11 extending from the first end 9a to a distance from the second end 9b. The diameter of the second bore 11 is larger than that of the first bore 10 and larger than the diameter of the rod 6. A substantially U-shaped recess 12 is provided in the rod receiving portion 9 which extends from the first end 9a towards the second end 9b, the diameter of the recess 12 being slightly larger than the diameter of the rod 6 in such a way that the rod 6 can be placed in the recess and can be guided therein. The recess 12 forms two free legs 12a, 12b, on which an internal thread 13 is provided. The internal thread can be a metric thread, a flat thread, a negative angle thread, a sawtooth thread, or any other thread type. Preferably, a thread form such as a flat thread or negative angle thread is used which prevents or reduces splaying of the legs 12a, 12b when the inner screw 7 is screwed-in. The depth of the recess 12 is such that the rod 6 and the inner screw 7 can be inserted between the legs. Between the bottom of the recess and the legs 12a, 12b, a flat section 14 is provided, forming the end of the bore 11.

As can be seen in FIGS. 1, 2, 3 and 6, cuts 24 are provided in the rod receiving portion on either end of the channel formed by the recess 12.

The rod receiving portion 9 of the receiving part body 5 further comprises a plurality of coaxial slits 15 extending from the second end 9b to a distance from the first end, wherein the distance corresponds approximately to the length of the internal thread 13. The slits 15 are open at the second end 9b and extend, as can be seen in particular in FIGS. 1, 3 and 6 through the flat section 14 and the substantially U-shaped recess 12. At least one slit 15, and preferably more than one slit, is provided on either side of the recess 12. The number of slits is provided according to the degree of flexibility which is to be provided by the slits. It may depend, for example, on the material and wall thickness and/or other factors.

Adjacent to the second end 9b the receiving part body 5 comprises a head receiving portion 16 providing an accommodation space for the head 3 of the bone anchoring element 1. The head receiving portion 16 has an outer surface which tapers towards the second end 9b and which has an open end 17 opposite to the second end 9b. The exterior surface of the head receiving portion 16 can be partly or fully tapered. It is tapered at least in the region of the largest diameter of the head 3. The open end 17 can have a rounded edge.

Figure 4:
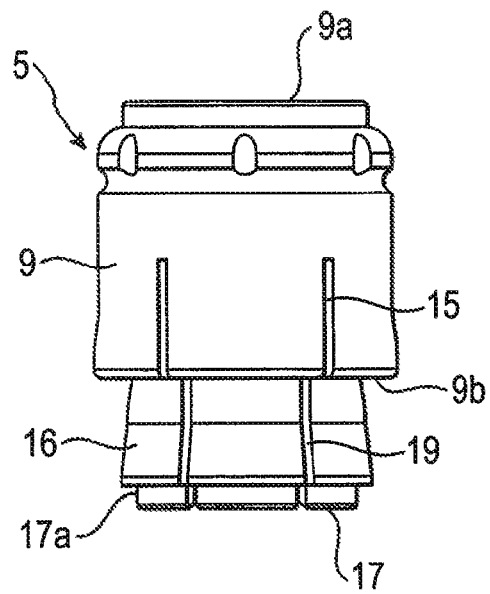
FIG. 4 shows a side view of the receiving part body of FIG. 3.
Figure 5:
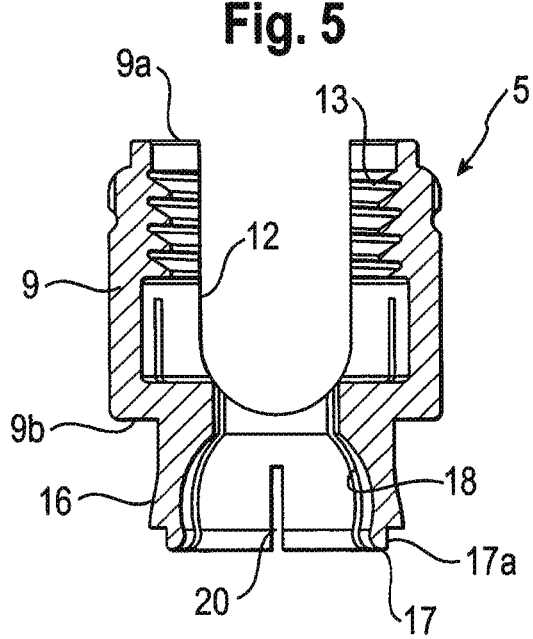
FIG. 5 shows a side view of the receiving part body of FIG. 4 rotated by 90°.
Figure 6:
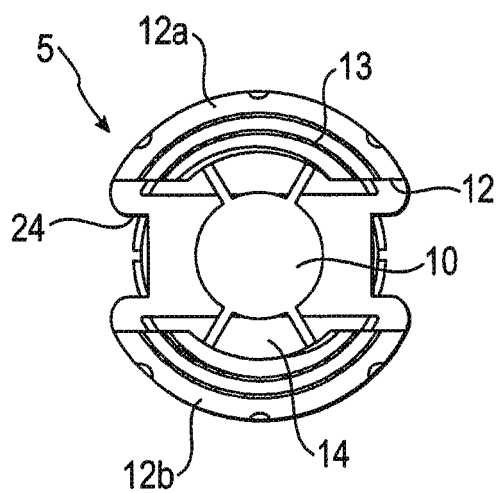
FIG. 6 shows a top view of the receiving part body of FIG. 3.
Figure 7:
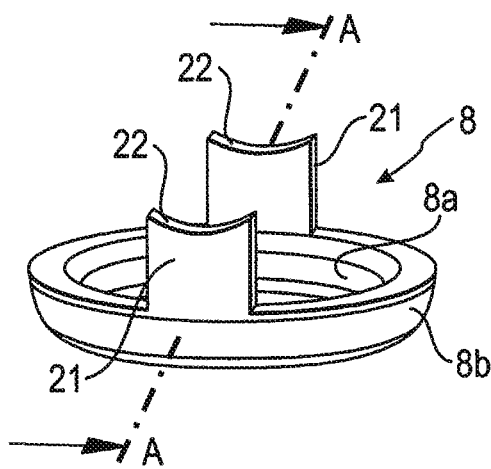
FIG. 7 shows a perspective view of the locking ring.
Figure 8:
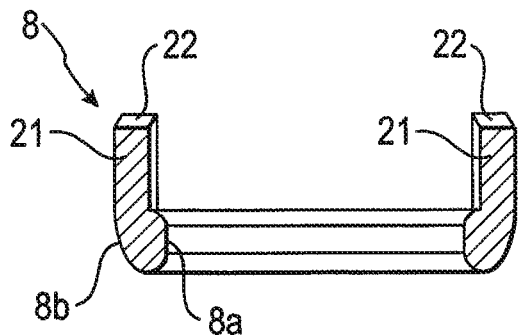
FIG. 8 shows a cross-sectional view of the locking ring of FIG. 7, the section being taken along line A-A.

As can be seen in particular in FIGS. 3 to 5, the outer diameter of the rod receiving portion 9 at the second end 9b is larger than the outer diameter of the head receiving portion 16 adjacent to the second end 9b, and is also larger than the outer diameter of the head receiving portion at the open end 17. Hence, the head receiving portion 16 is recessed with respect to the rod receiving portion 9.

As can be seen in particular in FIG. 5, the head receiving portion 16 has an internal hollow section 18 forming a seat for the head 3 of the bone anchoring element 1. The hollow section 18 is adapted in its shape to correspond to the shape of the head 3, in the embodiment shown it is a spherical section for accommodating the spherical head 3. The hollow section 18 is dimensioned in such a way that it encompasses the head 3 of the bone anchoring element from the side, covering a region including the largest diameter of the head 3.

A plurality of slits 19 are provided in the head receiving portion 16 which are open to the open end 17 and extend from the open end 17 to the second end 9b of the rod receiving portion, and some of which may continue into the slits 15 of the rod receiving portion 9, thereby forming continuous slits extending from the open end 17 of the head receiving portion 16 into the rod receiving portion 9. The number of slits 19 may be equal to the number of slits 15, however, the number of slits can be smaller or larger depending on the desired flexibility of the head receiving portion 16. In addition, slits 20 are provided on the side of the head receiving portion 16 which is adjacent to the substantially U-shaped recess 12 of the rod receiving portion, as shown in FIG. 3. The slits 20 end at a distance from the second end 9b. The flexibility of the head receiving portion 16 is such that the head 3 of the anchoring element can be inserted by expanding the head receiving portion 16 and can be clamped by compressing the head receiving portion 16. The slits 15 in the rod receiving portion facilitate mounting of the receiving part body 5 onto the head 3 manually.

As can be seen in particular in FIGS. 3 to 5, adjacent to the open end 17, the head receiving portion 16 has a recessed area 17a for accommodation of a pre-locking ring 80, to be described later. The recessed area 17a has, in the embodiment shown, the shape of a circular recess with a rectangular contour.

The locking ring 8 will now be described with reference to FIGS. 1, 2, 7 and 8. The locking ring 8 has a substantially cylindrical outer surface with an outer diameter corresponding substantially to the outer diameter of the rod receiving portion 9 of the receiving part 5. The height of the locking ring 8 in an axial direction is smaller than that of the head receiving portion 16 of the receiving part body 5, so that, as shown in particular in FIG. 2, there is a distance between the locking ring 8 and the second end 9b of the rod receiving portion 9, when the locking ring 8 is in the position in which the head 3 is locked.

The locking ring 8 has on its inner side a curved interior surface portion 8a. The curvature is directed to the center of the locking ring 8. The curved interior surface portion 8a can have a spherical curvature. Other types of curvatures are also possible. The radius of the curvature is smaller than the radius of the head 3. The dimensions of the locking ring 8 with respect to its inner portions are such that the locking ring 8 can slide along the outer surface of the head receiving portion 16, thereby increasingly compressing the head receiving portion 16 when sliding downward.

The locking ring 8 further has on its side facing the second end 9b two projections 21 located diametrically opposite to each other. The projections 21 have a height such that they project above the bottom of the substantially U-shaped recess 12 and extend into the cuts 24 when the locking ring 8 is in a position in which the head 3 is not yet clamped. The free end 22 of the projections 21 can be curved, particularly inwardly curved, with a curvature corresponding to that of the rod 6. The locking ring is arranged in such a way around the head receiving portion 16 of the receiving part body 5 that the projections 21 are located at the positions of the recess 12. By means of this, the projections 21 which project into the recess 12 prevent the locking ring 8 from rotating when the rod 6 is not inserted.

The flexibility of the head receiving portion 16 and the size of the head receiving portion at the open end 17 allows mounting of the locking ring 8 by assembling it from the free end 17 onto the head receiving portion 16. Since the outer diameter of the head receiving portion is smaller than that of the rod receiving portion 9, the locking ring 8 does not project or only minimally project beyond the rod receiving portion in a radial direction. The locking ring 8 may have a tapered exterior surface 8b as shown in FIG. 11 to further reduce its diameter in a direction of the open end 17.

Figure 9:
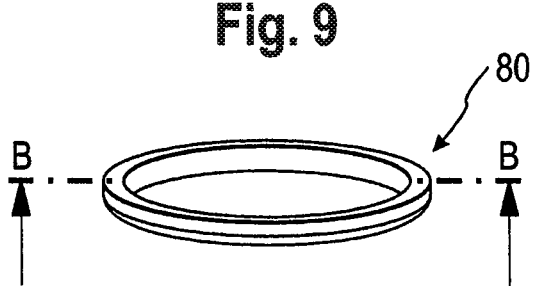
FIG. 9 shows a perspective view of the pre-locking ring.
Figure 10:
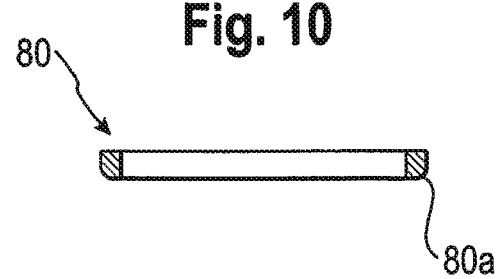
FIG. 10 shows a cross-sectional view of the pre-locking ring of FIG. 9, the section being taken along line B-B.

The pre-locking ring is now explained with respect to FIGS. 1, 2, 9 and 10. The pre-locking ring 80 has a substantially rectangular cross section as shown in FIGS. 9 and 10, wherein the lower outer edge 80a may be rounded. The inner diameter of the pre-locking ring is slightly smaller than the outer diameter of the recess 17a provided at the open end 17 of the head receiving portion 16. The dimensions of the recess 17a and the pre-locking ring 80 are such that when the pre-locking ring 80 is mounted onto the head receiving portion 16 from the open end 17 it slightly compresses the head receiving portion 16 so that the head 3 of the bone anchoring element is pre-locked by the pre-stress exerted by the pre-locking ring. Pre-locking means that under conditions arising during surgery the angular position of the bone anchoring element 1 with respect to the receiving part body 5 is maintained in a temporary position and can be loosened only by exerting an additional force onto the receiving part body or the bone anchoring element.

In the embodiment shown and depicted in an enlarged view in FIG. 11, the inner contour 80b of the pre-locking ring 80 is rectangular to fit into the rectangular recess 17a of the head receiving portion 16. Other geometries are also possible. For example, as shown in the embodiment of FIG. 12, the inner contour 80b' of the locking ring 80' can be rounded. As shown in the embodiment of FIG. 13, the recess 17a' at the open end 17 of the head receiving portion can be tapered and the contour 80b" of the pre-locking ring 80" can be tapered to fit to the contour of the recess 17a'. As shown in the embodiment of FIG. 14, the recess 17a" can be circular-shaped and the pre-locking ring 80" has a circular cross-section which fits into the recess. Various other shapes are also conceivable.

The inner screw 7 has a thread corresponding to the internal thread 13 provided on the legs. If a thread form which prevents the legs from splaying is used, a single closure element such as the inner screw 7 is sufficient. This reduces the size of the bone anchoring device in a radial direction. Other closure elements such as, for example, an outer nut, are also possible.

The receiving part body 5, the locking ring 8, the inner screw 7 and the bone anchoring element 1 are made of a bio-compatible material, for example, of titanium or a stainless steel or bio-compatible alloy or bio-compatible plastic material with sufficient strength. The pre-locking ring is also made of one of these materials. However, the pre-locking ring 80 can also be made from a material which exhibits elastic properties, such as, for example, an elastomer material. For example, the pre-locking ring 80 can be made of an elastomer material which exhibits properties similar to that of an O-ring or other kinds of rubber rings.

The bone anchoring device may be preassembled with the locking ring 8 mounted on the head receiving portion 16 of the receiving part body 5 and with the screw head 3 inserted and the pre-locking ring 80 mounted in the recess 17a.

The function of the bone anchoring device with respect to the locking of the head is now explained with reference to FIGS. 15 to 17. FIG. 15 shows a first condition in which the locking ring 8 is in a first position $P_1$ near the second end 9b of the rod receiving portion 9 of the receiving part body 5. The head 3 of the bone anchoring element is not yet inserted into the hollow space 18 and the pre-locking ring 80 is not yet mounted. Means can be provided (not shown) which releaseably hold the locking ring 8 in the position $P_1$. Such means can be, for example, a catch engaging a groove.

As shown in FIG. 16, after inserting the head 3 of the bone anchoring element and mounting the pre-locking ring 80, the head 3 is held in the head receiving portion 16 in a pre-locked condition due to the pre-stress exerted by the pre-locking ring 80 onto the head receiving portion 16. In this condition, a pivoting of the head 3 within the head receiving portion is only possible by exerting an additional force to move the receiving part body 5 relative to the head 3. When the pre-locking ring 80 is mounted, a removal of the head 3 from the head receiving portion 16 is no longer possible.

As shown in FIG. 17, for final locking of the head 3 within the head receiving portion the locking ring 8 is moved downwards. This can be accomplished, for example, when the inner screw 7 presses onto the rod 6 and the rod presses onto the locking ring 8 via the projections 21. In the course of tightening the inner screw 7 the locking ring 8 is shifted downward until the curved portion 8a engages the tapered exterior surface portion of the head receiving portion 16. When the locking ring is at a position of the greatest diameter of the head 3 in a direction of the screw axis of the bone anchoring device, the pressure exerted by the curved portion 8a of the locking ring onto the head receiving portion 16 is largest, whereby the head 3 is clamped in such a way that it is locked. Simultaneously, a further downward movement of the locking ring 8 is prevented.

The bone anchoring device can be preassembled either by the manufacturer or in the course of preparation of the surgery or at any other time. Advantageously, the surgeon selects prior to surgery the necessary receiving parts and bone anchoring elements according to the specific requirements of the clinical application. The design of the bone anchoring device allows selection of an appropriate bone anchoring element in terms of diameter, length and other features of the anchoring section. Hence, a modular system is provided which includes receiving parts and several bone anchoring elements, which then individually can be chosen and adapted.

In the pre-locking condition the head 3 remains clamped due to the pre-locking ring 80 when the inner screw 7 is loosened. This allows further adjustments of the rod 6.

In use, the preassembled bone anchoring device is screwed into the bone. The recess 4 of the head can be accessed with a screw tool through the first bore 10. The locking ring 8 is in its first position $P_1$ close to the second end 9b where it does not clamp the head 3. The head 3 is, however, pre-locked by means of the pre-locking ring 80. To correctly align the receiving part with respect to the rod to which it shall be connected, an additional force is exerted onto the receiving part either manually or by application of an instrument. Once the correct position of the rod with respect to other bone anchoring devices is achieved, the inner screw 7 is screwed between the legs until it presses onto the rod. The rod is pressed against the bottom of the substantially U-shaped recess 12 thereby engaging the free ends 22 of the projections 21, respectively, and shifting down the locking ring 8. When the locking ring 8 is moved towards the free end 17 of the head receiving portion it compresses the head receiving portion, thereby locking the head. Since the force which is exerted by the locking ring 8 acts with the interior curved surface 8a from the lateral side, the force utilized for safely immobilizing the head is smaller than when a force acts from above the head 3. This also allows for reducing the size of the device by allowing a wall thickness of the receiving part to be reduced. Final tightening of the inner screw locks the rod and the head substantially simultaneously.

Further modifications of the embodiment shown are possible. For example, the head of the bone anchoring element can have any other shape, such as, for example, a cylindrical shape, whereby a monoaxial bone screw is provided allowing rotation of the screw element with respect to the receiving part around a single axis. The head 3 can also be conically shaped or otherwise shaped, where the internal hollow section 18 of the head receiving portion 16 is adapted to any such shape. In a further modification, the receiving part body 5, or at least the head receiving portion 16, is made of bio-compatible plastic material which provides for elasticity to a certain degree. In this case, slits may be omitted.

The projections of the locking ring which engage the rod can have various other shapes. For example, the surface of the free end can be flat or be otherwise shaped. In some embodiments, the projections can be omitted.

The head receiving portion can have an inclined open end 17 to allow for a greater angulation of the head in one direction.

In one embodiment, the pre-locking ring 80 is made of a material exhibiting elasticity, and it may be possible to first mount the pre-locking ring 80 before inserting the head 3 of the bone anchoring element.

In one embodiment, the outer surface of the head receiving portion 16 can be spherical and the inner surface of the locking ring 8 can be tapered.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
a receiving part body comprising:
a rod receiving portion with a channel for receiving a rod, and
a head receiving portion for accommodating a head of a bone anchoring element, the head receiving portion having an open end and being flexible for inserting and clamping of the head;
a locking ring around the head receiving portion to exert a first force onto the head receiving portion to lock the head therein when the receiving part is in a locking position; and
a pre-locking ring separate from the locking ring and around the head receiving portion to exert a second force less than the first force onto the head receiving portion to clamp the head when the receiving part is in a temporary pre-locking position different from the locking position.

2. The receiving part of claim 1, wherein the pre-locking ring is held around the head receiving portion by the second force exerted onto the head receiving portion.

3. The receiving part of claim 1, wherein a longitudinal axis extends from the rod receiving portion to the head receiving portion, and wherein in the pre-locking position, the locking ring is movable along the longitudinal axis.

4. The receiving part of claim 1, wherein the pre-locking ring is prevented from moving toward the locking ring by a stop.

5. The receiving part of claim 1, wherein the pre-locking ring is arranged near the open end of the head receiving portion.

6. The receiving part of claim 1, wherein the pre-locking ring is configured to be mounted from the open end of the head receiving portion.

7. The receiving part of claim 1, wherein the pre-locking ring comprises an elastic material.

8. The receiving part of claim 1, wherein the head receiving portion has an exterior surface with a tapered portion and the locking ring has an interior surface with a curved portion having a convex curvature.

9. The receiving part of claim 1, wherein a height of the locking ring in a direction of a longitudinal axis of the receiving part is smaller than a height of the head receiving portion in the direction of the longitudinal axis of the receiving part.

10. The receiving part of claim 1, wherein the locking ring is configured to move upon exerting a pressure on the locking ring via the rod.

11. The receiving part of claim 1, wherein the rod receiving portion has a first end and a second end, and a recess extends from the first end in the direction of the second end to form the channel.

12. The receiving part of claim 1, wherein the rod receiving portion has a first end and a second end, and the head receiving portion is arranged at the side of the second end, and wherein the outer diameter of the head receiving portion adjacent to the second end is smaller than an outer diameter of the rod receiving portion at the second end.

13. The receiving part of claim 1, wherein the receiving part body comprises a plurality of slits adjacent to the open end.

14. The receiving part of claim 13, wherein at least one of the plurality of slits extends continuously from the open end of the head receiving portion into the rod receiving portion.

15. The receiving part of claim 1, wherein the pre-locking ring has an inner contour forming at least one right angle configured to contact the head receiving portion.

16. The receiving part of claim 1, wherein the pre-locking ring has a rounded inner contour configured to contact the head receiving portion.

17. The receiving part of claim 16, wherein the pre-locking ring has a circular cross-section.

18. The receiving part of claim 1, wherein the pre-locking ring has an inner contour with a portion that is tapered relative to a central axis of the pre-locking ring.

19. The receiving part of claim 1, wherein the pre-locking ring has a different shape while in a neutral position than a shape of the locking ring while in a neutral position.

20. A bone anchoring device comprising:
- a bone anchoring element having a threaded shaft and a head; and
- a receiving part for receiving a rod for coupling the rod to the bone anchoring element, the receiving part comprising:
  - a receiving part body comprising a rod receiving portion with a channel for receiving the rod, and a head receiving portion for accommodating the head of the bone anchoring element, the head receiving portion having an open end and being flexible for inserting and clamping of the head;
  - a locking ring around the head receiving portion to exert a first force onto the head receiving portion to lock the head therein when the receiving part is in a locking position; and
  - a pre-locking ring separate from the locking ring and around the head receiving portion to exert a second force less than the first force onto the head receiving portion to clamp the head when the receiving part is in a temporary pre-locking position different from the locking position.

21. The bone anchoring device according to claim 20, further comprising a closure element for securing the rod in the channel.

22. The bone anchoring device according to claim 21, wherein the closure element comprises an inner screw.

23. The bone anchoring device of claim 20, wherein in the pre-locking position, the second force temporarily holds the bone anchoring element at an adjustable angular position relative to the receiving part.

24. A method of coupling a rod to a bone anchoring element via a receiving part, the receiving part comprising a receiving part body comprising a rod receiving portion with a channel for receiving the rod and a head receiving portion having an open end and being flexible for inserting and clamping of a head of the bone anchoring element, a locking ring around the head receiving portion, and a pre-locking ring separate from the locking ring and around the head receiving portion, the method comprising:
- introducing the head of the bone anchoring element into the open end of the head receiving portion;
- mounting the pre-locking ring around the head receiving portion, wherein the pre-locking ring exerts a first force onto the head receiving portion to clamp the head and to temporarily hold a position of the receiving part relative to the bone anchoring element when the receiving part is in a pre-locking position;
- pivoting the head receiving portion relative to the head to align the receiving part with the rod;
- inserting the rod into the channel of the rod receiving portion;
- advancing a closure element in the channel to push the rod against the locking ring; and
- further advancing the closure element in the channel towards the head receiving portion to force the locking ring towards the open end of the head receiving portion via the rod to adjust the receiving part to a locking position different from the pre-locking position, wherein the locking ring exerts a second force greater than the first force onto the head receiving portion to lock the position of the bone anchoring element relative to the receiving part.

25. The method of claim 24, wherein a minimum force for pivoting the head receiving portion relative to the head after the mounting of the pre-locking ring around the head receiving portion is greater than a minimum force for pivoting the head receiving portion relative to the head prior to the mounting of the pre-locking ring around the head receiving portion.

* * * * *